(12) United States Patent
Straub

(10) Patent No.: US 8,114,106 B2
(45) Date of Patent: *Feb. 14, 2012

(54) CATHETER FOR ASPIRATING, FRAGMENTING AND REMOVING MATERIAL

(75) Inventor: Immanuel Straub, Wangs (CH)

(73) Assignee: Straub Medical AG, Wangs (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/030,165

(22) Filed: Feb. 18, 2011

(65) Prior Publication Data

US 2011/0160758 A1    Jun. 30, 2011

Related U.S. Application Data

(63) Continuation of application No. 10/591,100, filed as application No. PCT/IB2005/000543 on Mar. 3, 2005, now Pat. No. 7,905,896.

(30) Foreign Application Priority Data

Mar. 4, 2004 (CH) ........................ 0369/04
Dec. 22, 2004 (CH) ........................ 2176/04

(51) Int. Cl.
*A61B 17/32* (2006.01)

(52) U.S. Cl. .................. 606/170; 606/180; 606/159

(58) Field of Classification Search .................. 604/22, 604/35, 70, 531; 606/84, 159, 198, 170, 606/180, 128, 194, 110, 114, 115, 127
See application file for complete search history.

(56) References Cited

U.S. PATENT DOCUMENTS

| | | |
|---|---|---|
| 2,026,630 A | 1/1936 | Harris |
| 3,082,805 A | 3/1963 | Royce |
| 3,732,858 A | 5/1973 | Banko |
| 3,945,375 A | 3/1976 | Banko |
| 4,705,511 A | 11/1987 | Kocak |
| 4,844,064 A | 7/1989 | Thimsen et al. |

(Continued)

FOREIGN PATENT DOCUMENTS

DE    10162933 A1    7/2003

(Continued)

OTHER PUBLICATIONS

English translation of the Written Opinion of the International Search Authority for parent International Application No. PCT/IB2005/000543, Sep. 11, 2007.

(Continued)

*Primary Examiner* — Ryan Severson
*Assistant Examiner* — David Eastwood
(74) *Attorney, Agent, or Firm* — Matthew B. Dernier, Esq.; Gibson & Dernier, LLP

(57) ABSTRACT

Catheter for aspiration, fragmentation and removal of removable material from hollow bodies, in particular of thrombi and emboli from human blood vessels, comprising a working head, a flexible transport screw, a flexible tube, and a cutting tool. The working head is independently displaceable along a guide wire, is arranged at the distal end of the catheter, and has at least one lateral opening. The flexible transport screw can be rotated at a distance by means of a rotary drive of a drive unit. The flexible tube surrounds the transport screw, is connected to the working head, and is intended for removing the detached thrombi and emboli fragments. The transport screw forms a shearing cutting tool in cooperation with the lateral opening of the working head, in order to comminute the detached thrombi and emboli between peripheral borders of the transport screw and borders of the lateral opening.

24 Claims, 18 Drawing Sheets

U.S. PATENT DOCUMENTS

| | | | |
|---|---|---|---|
| 4,857,046 A | 8/1989 | Stevens et al. | |
| 4,867,157 A | 9/1989 | McGurk-Burleson et al. | |
| 4,935,025 A | 6/1990 | Bundy et al. | |
| 5,078,723 A | 1/1992 | Dance et al. | |
| 5,084,052 A | 1/1992 | Jacobs | |
| 5,100,426 A | 3/1992 | Nixon | |
| 5,226,909 A | 7/1993 | Evans et al. | |
| 5,312,425 A | 5/1994 | Evans et al. | |
| 5,417,703 A | 5/1995 | Brown et al. | |
| 5,569,178 A | 10/1996 | Henley | |
| 5,571,122 A | 11/1996 | Kelly et al. | |
| 5,833,704 A | 11/1998 | McCombs et al. | |
| 5,873,882 A | 2/1999 | Straub et al. | |
| 6,217,565 B1 | 4/2001 | Cohen | |
| 6,565,588 B1 | 5/2003 | Clement et al. | |
| 2002/0010487 A1 | 1/2002 | Evans et al. | |
| 2003/0114875 A1 | 6/2003 | Sjostrom | |

FOREIGN PATENT DOCUMENTS

| | | | |
|---|---|---|---|
| EP | 0310285 | A2 | 4/1989 |
| EP | 0448859 | A2 | 10/1991 |
| EP | 0448859 | A3 | 5/1992 |
| EP | 0267539 | B1 | 4/1993 |
| EP | 0582533 | A1 | 2/1994 |
| EP | 0669106 | A1 | 8/1995 |
| EP | 0680730 | A2 | 11/1995 |
| EP | 0680730 | A3 | 1/1996 |
| EP | 0739603 | A1 | 10/1996 |
| EP | 0669106 | B1 | 2/1999 |
| EP | 0739603 | B1 | 8/2001 |
| JP | H05-78207 | U | 10/1993 |
| JP | H10-277047 | A | 10/1998 |
| JP | H11-506358 | A | 6/1999 |
| JP | 2002-538876 | A | 11/2002 |
| JP | 2005-512631 | A | 5/2005 |
| WO | 91/01114 | A | 2/1991 |
| WO | 94/24941 | A1 | 11/1994 |
| WO | 96/29941 | A1 | 10/1996 |
| WO | 00/47116 | A1 | 8/2000 |
| WO | 00/54659 | A1 | 9/2000 |
| WO | 02/49690 | A2 | 6/2002 |
| WO | 02/49690 | A3 | 6/2002 |
| WO | 2005/084562 | A3 | 9/2005 |
| WO | 2010/061308 | A1 | 6/2010 |

OTHER PUBLICATIONS

Copending U.S. Appl. No. 13/129,951, filed May 18, 2011.
International Search report for related PCT/IB2009/054909, dated Mar. 4, 2010.
English translation of the IPRP and Written Opinion of the International Search Authority for for related PCT/IB2009/054909, dated Jun. 9, 2011.

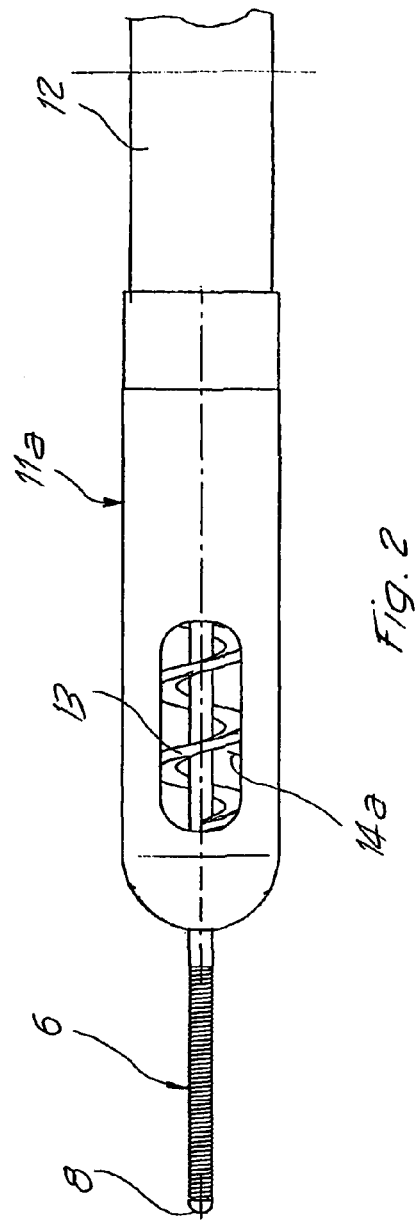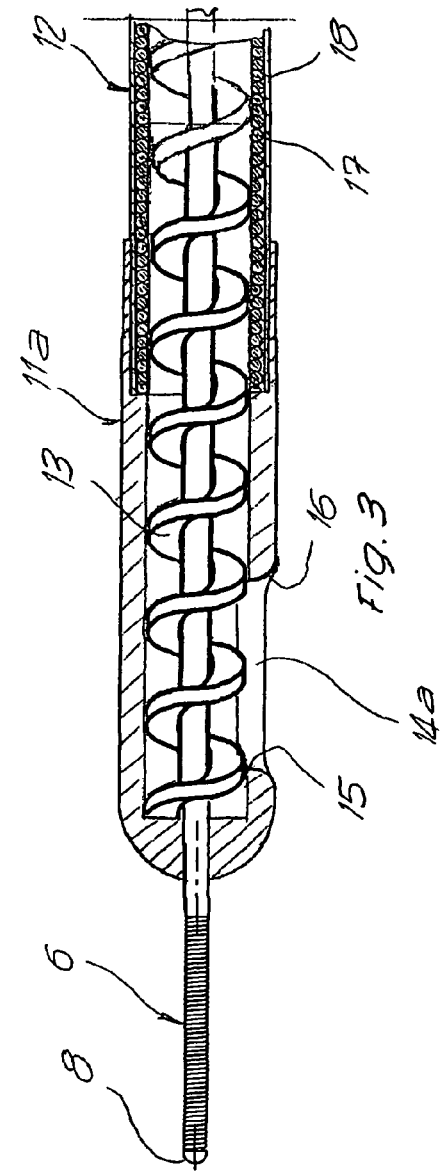

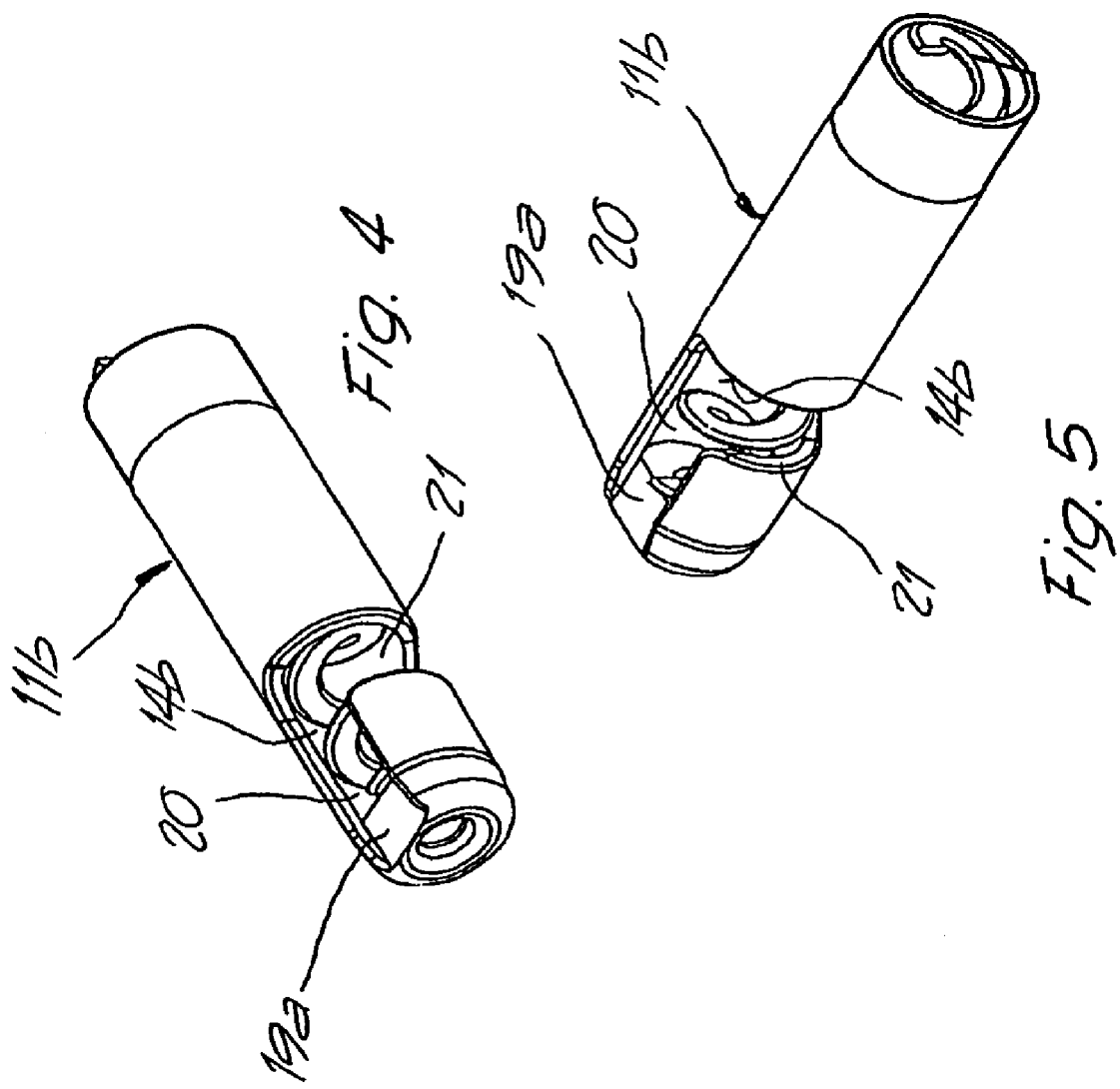

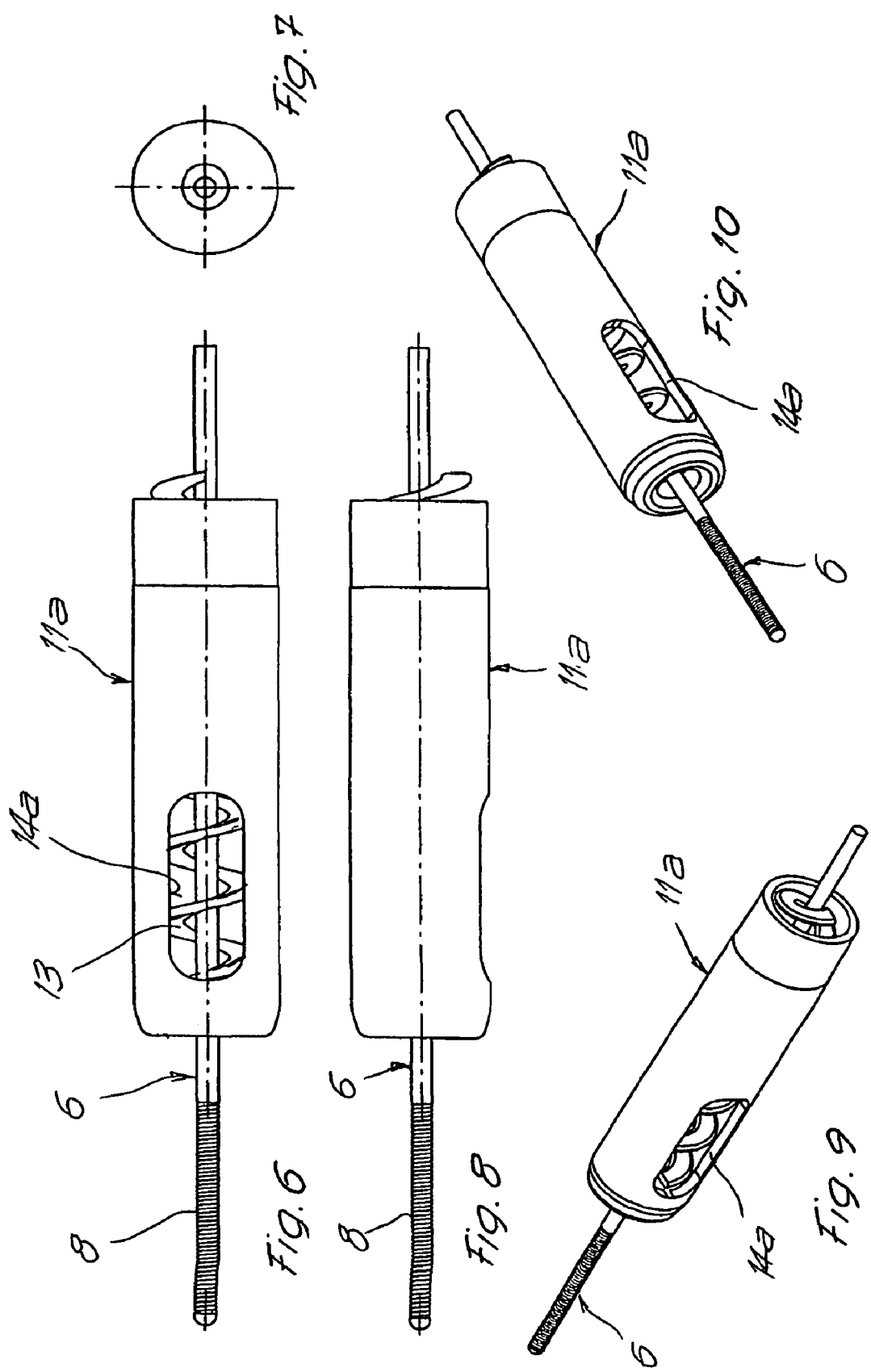

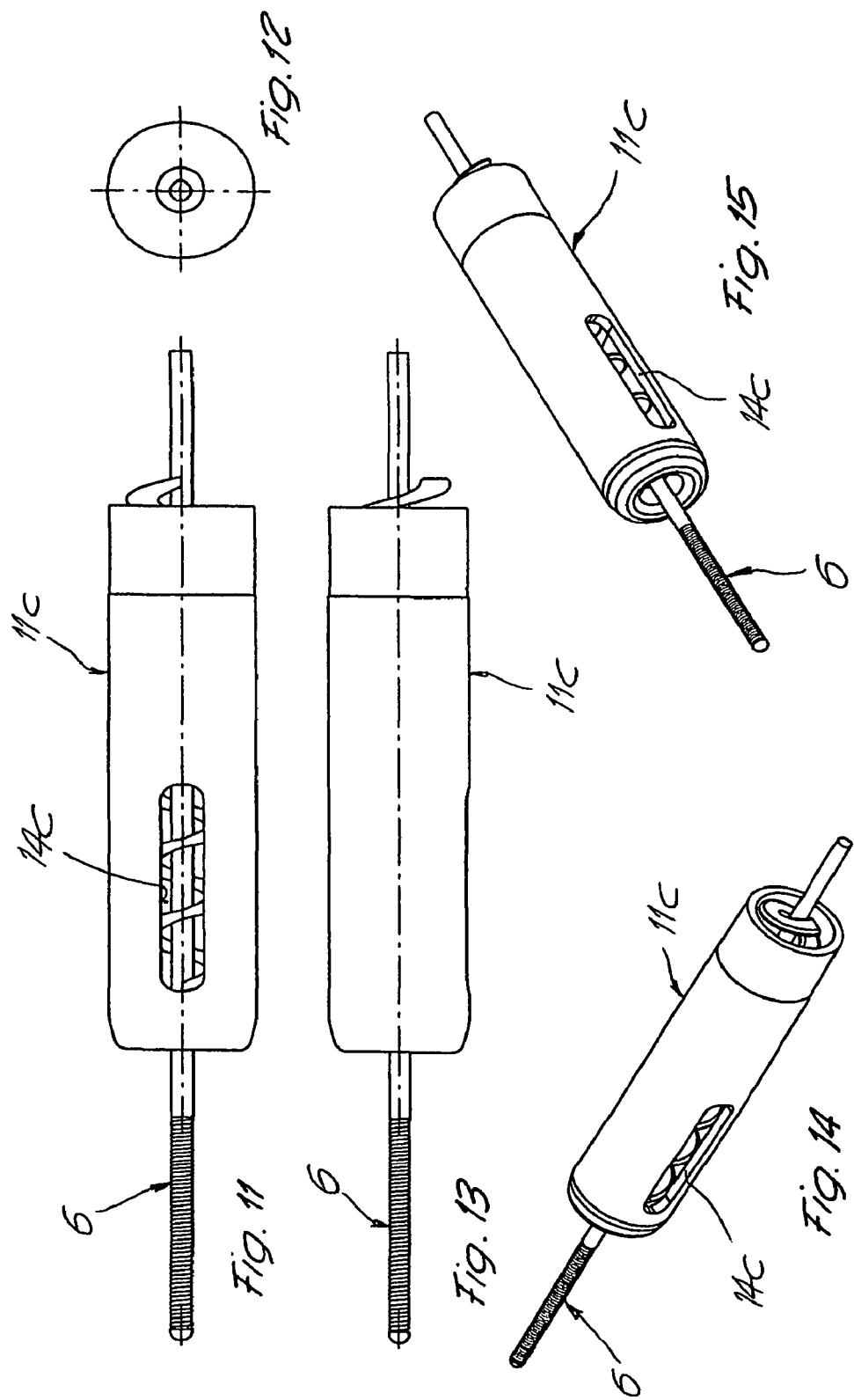

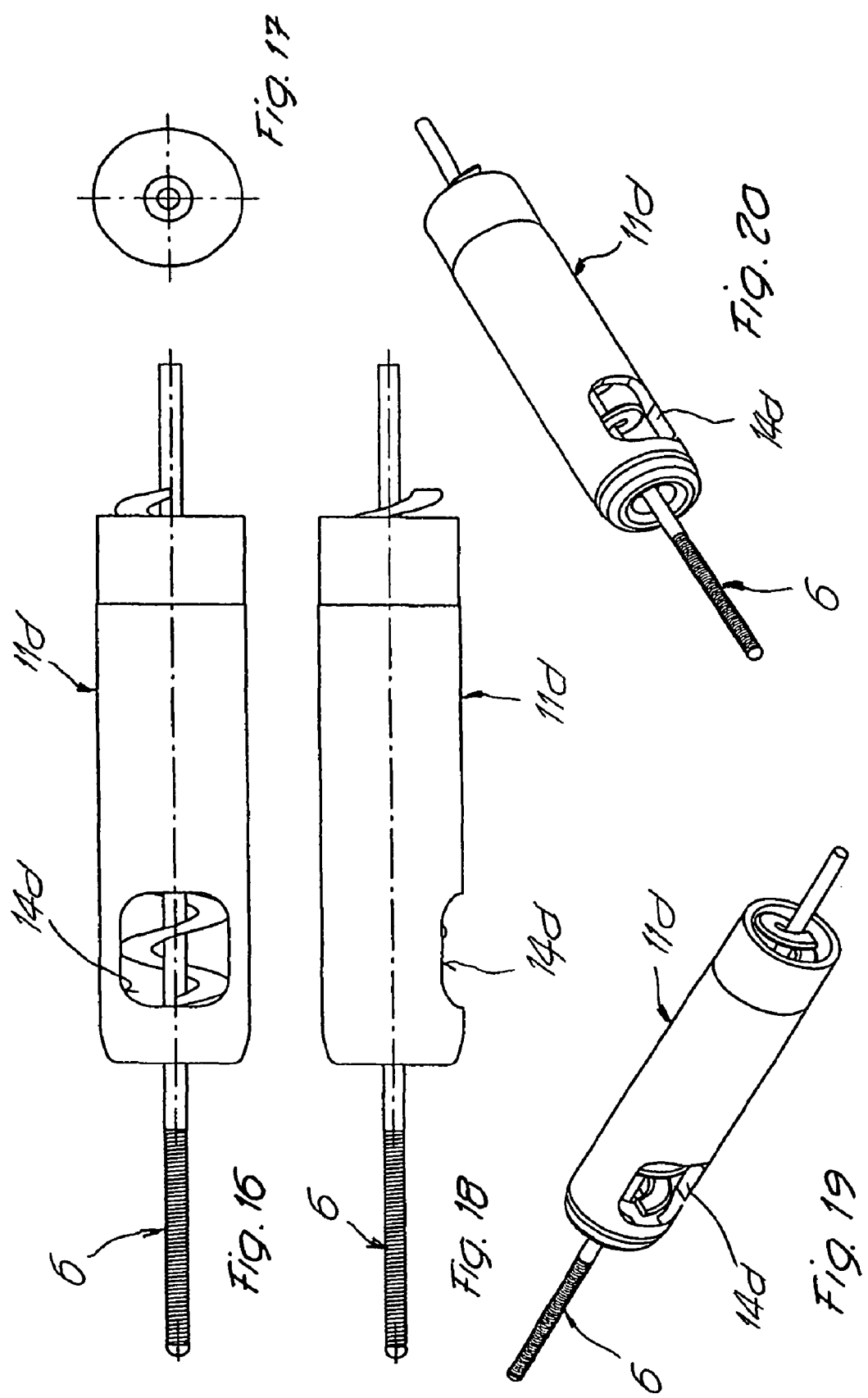

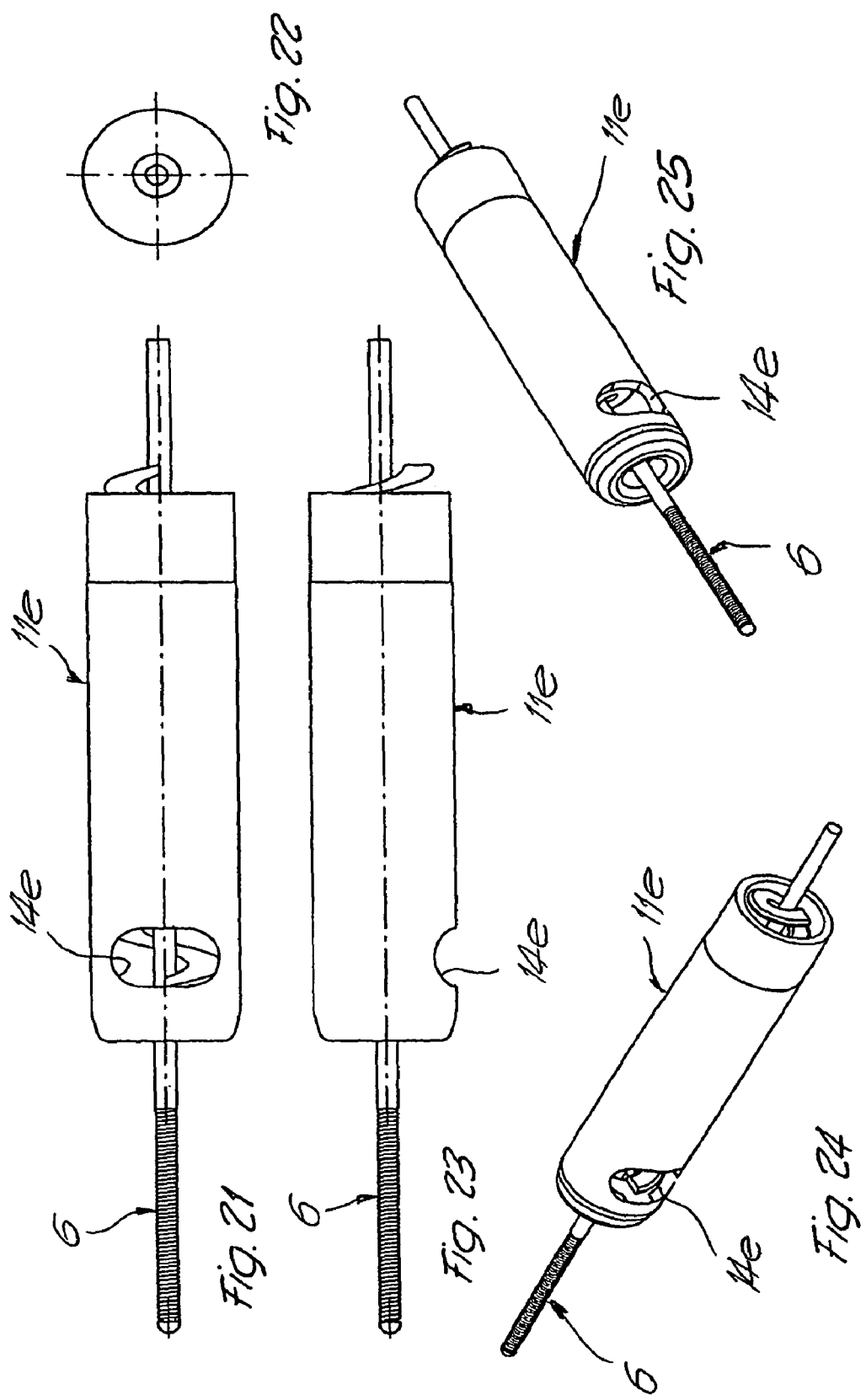

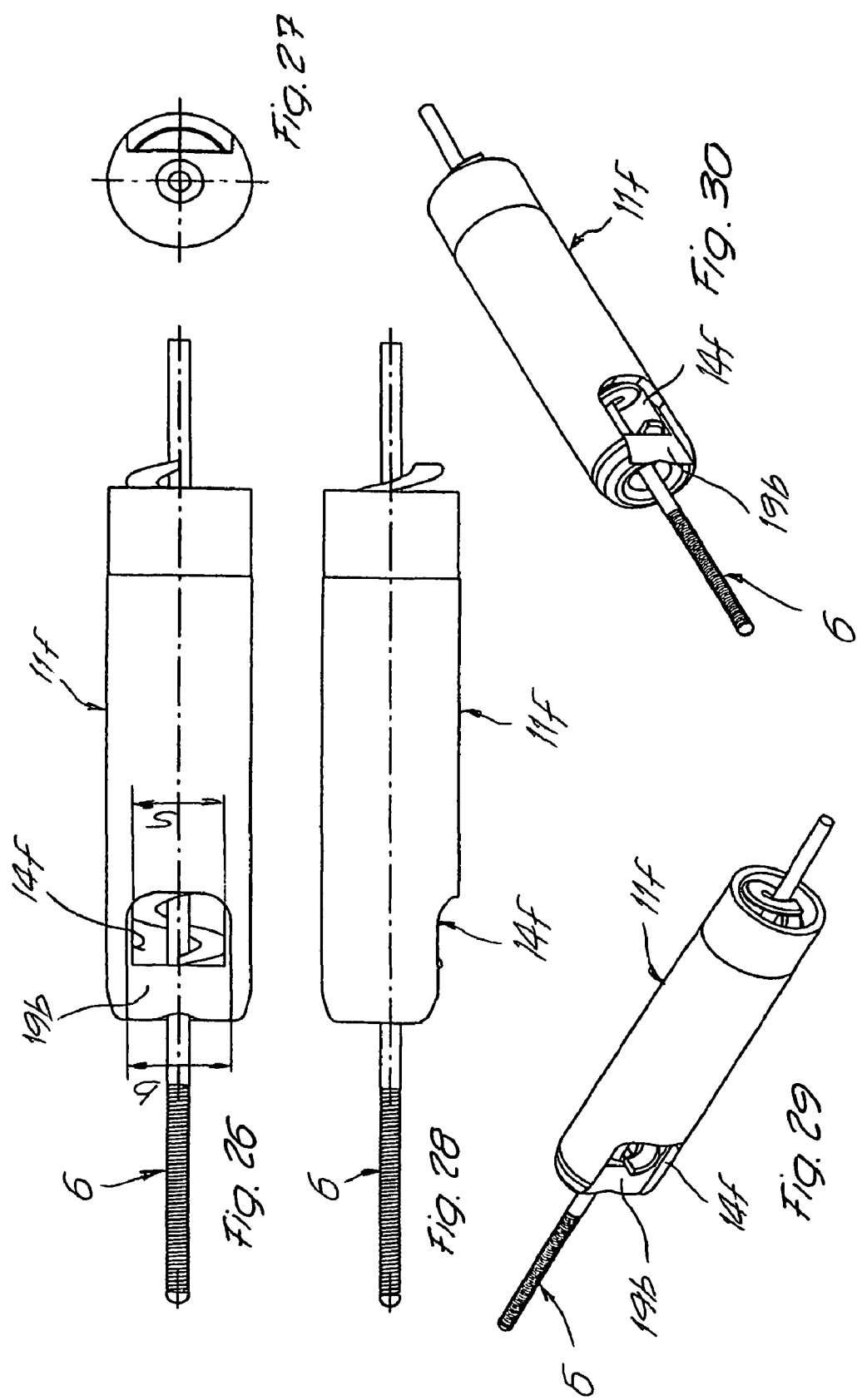

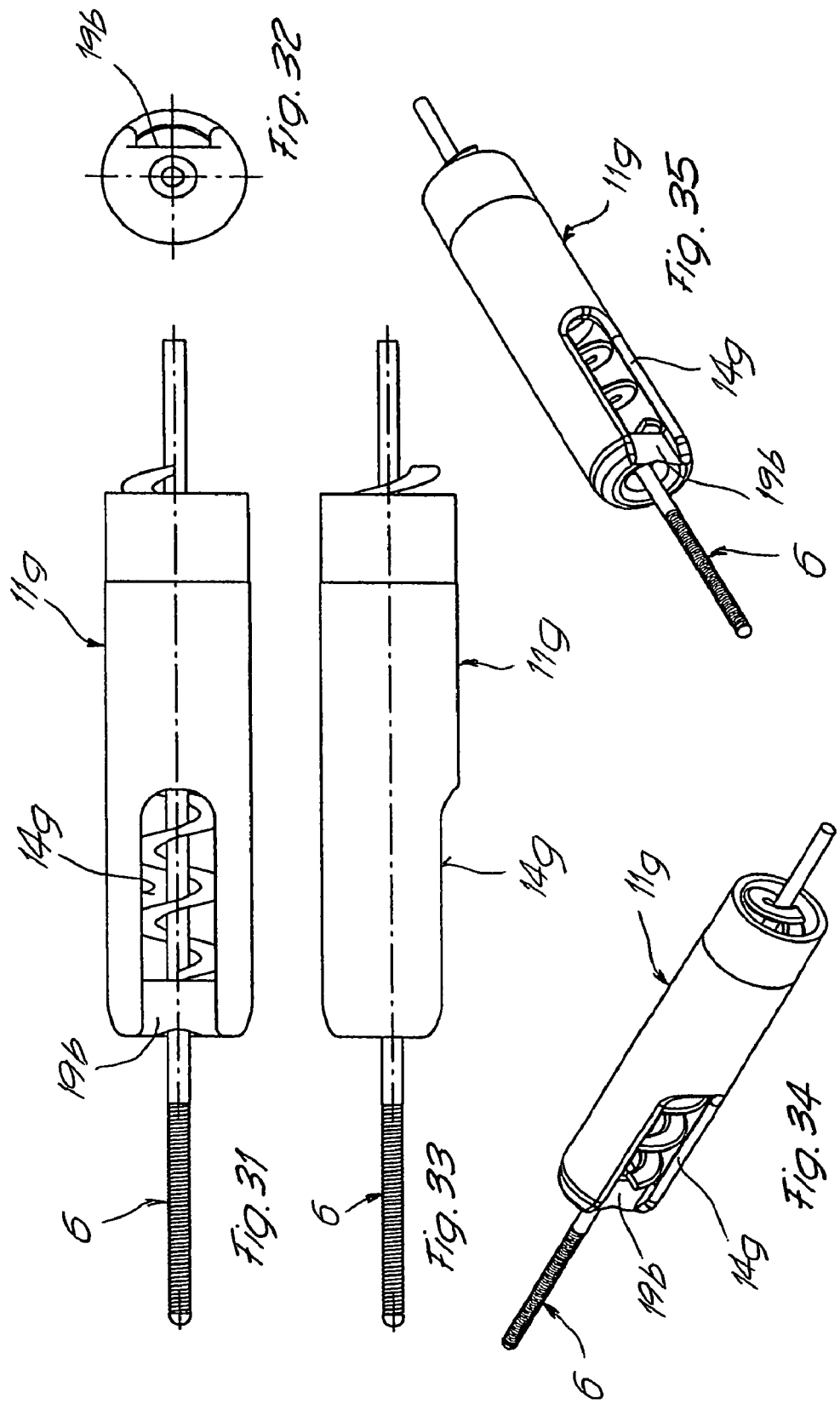

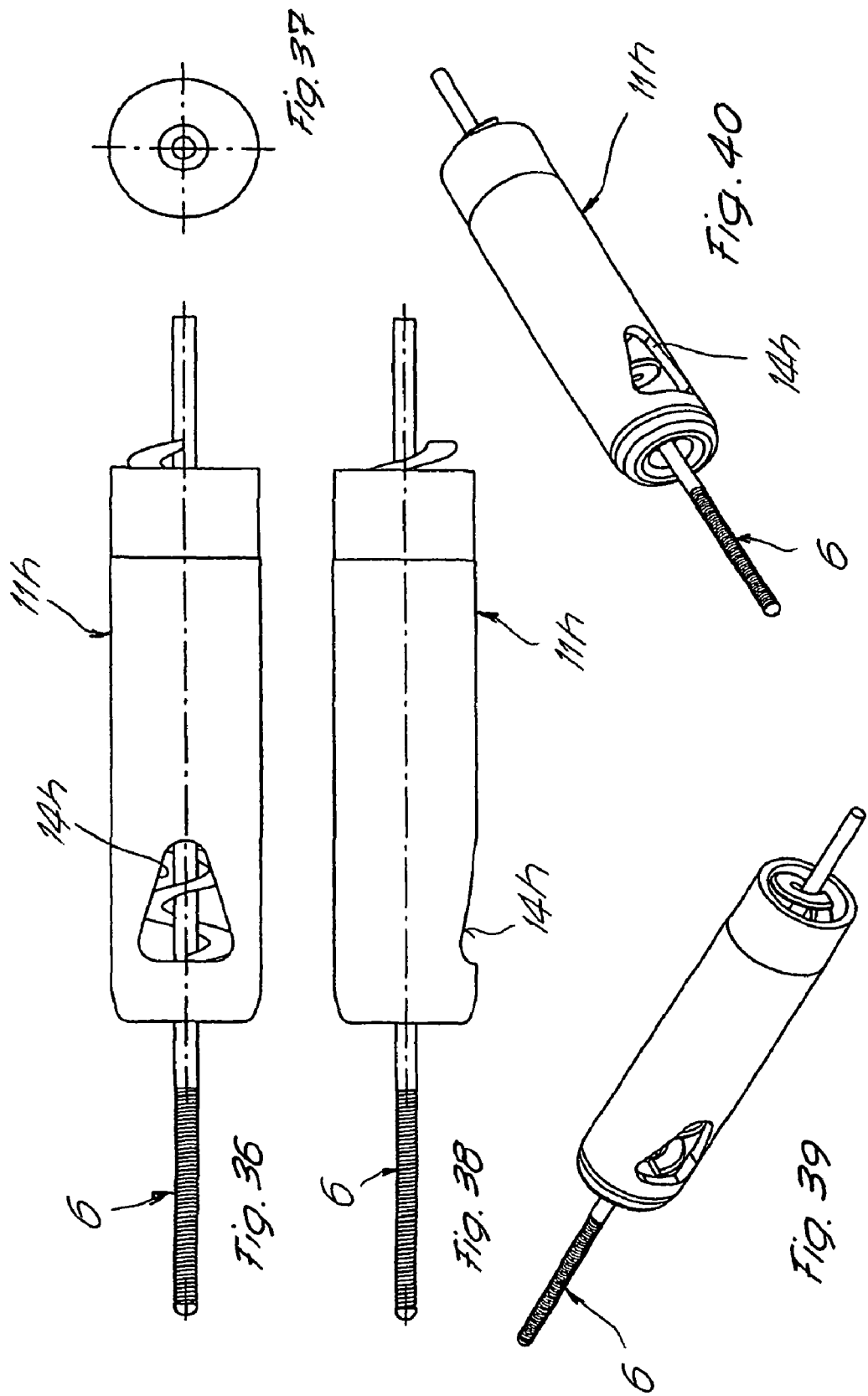

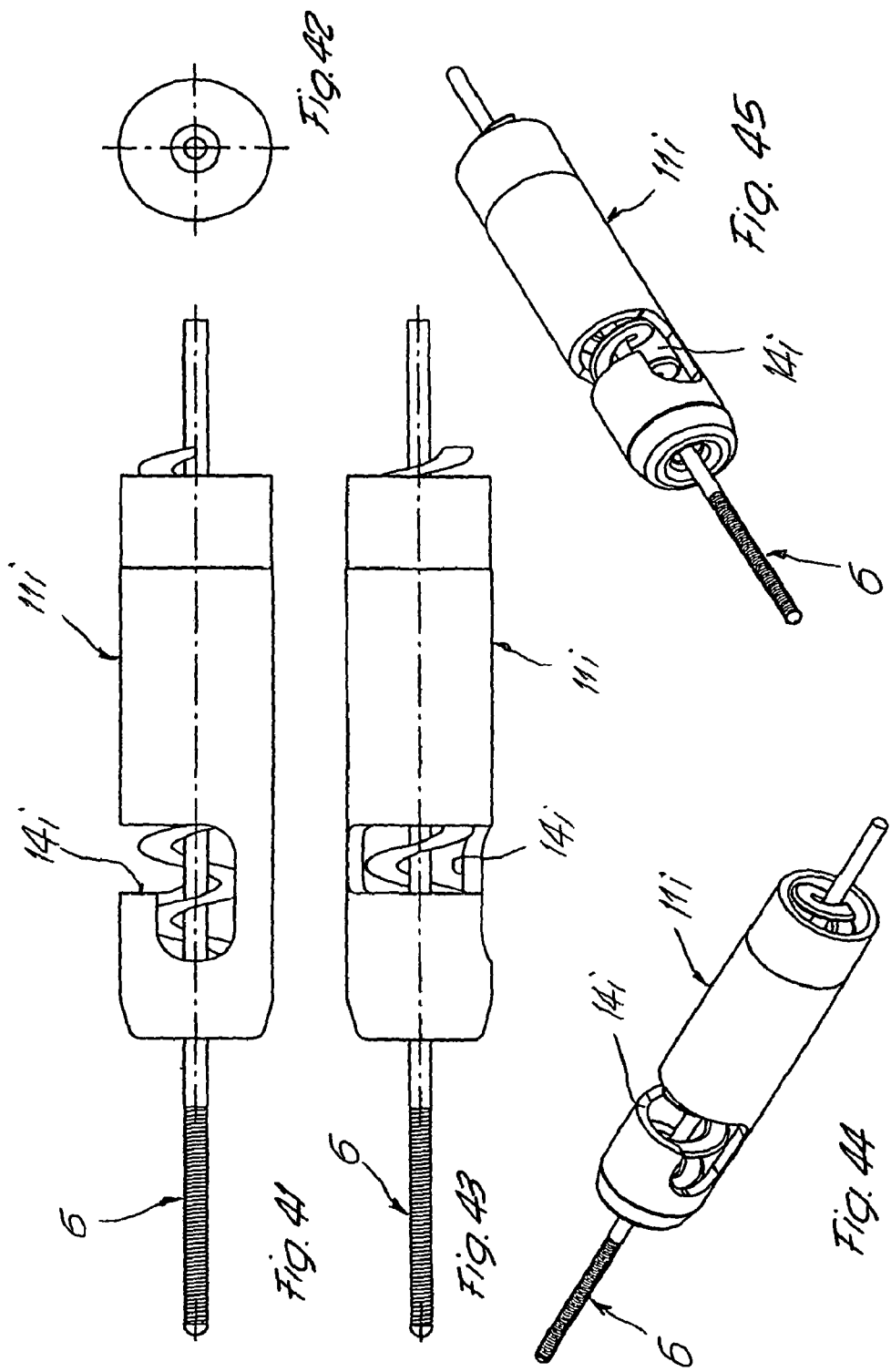

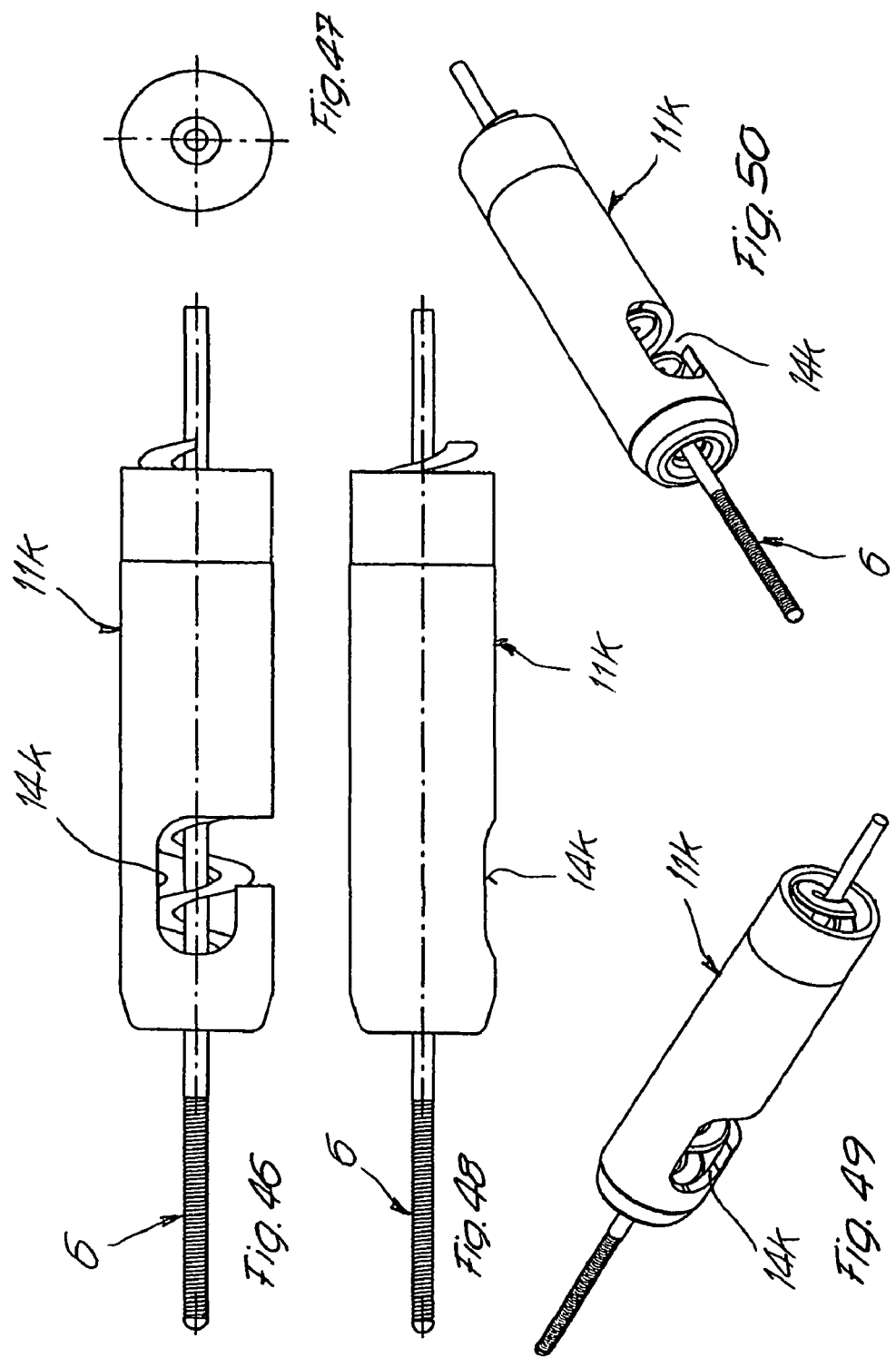

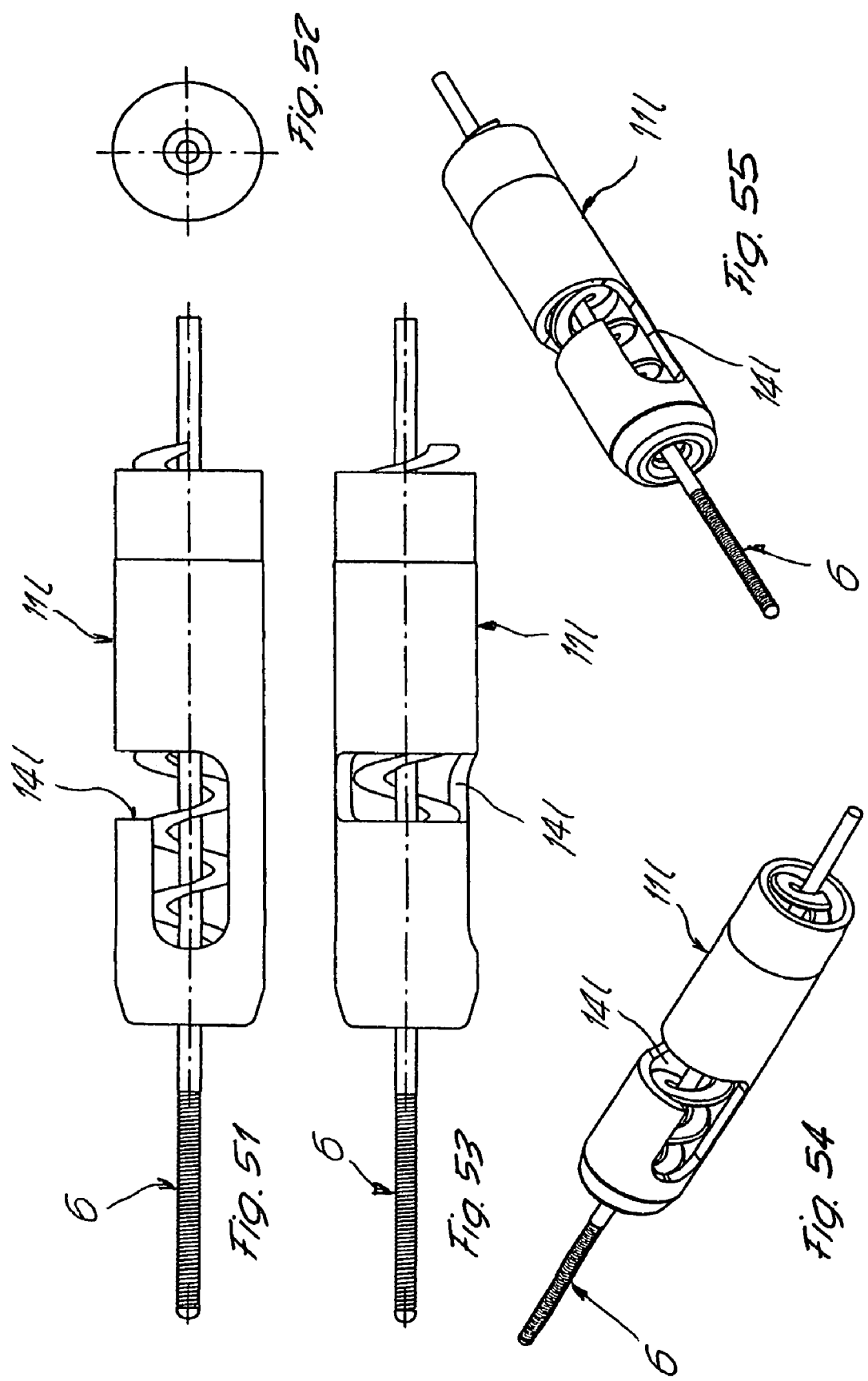

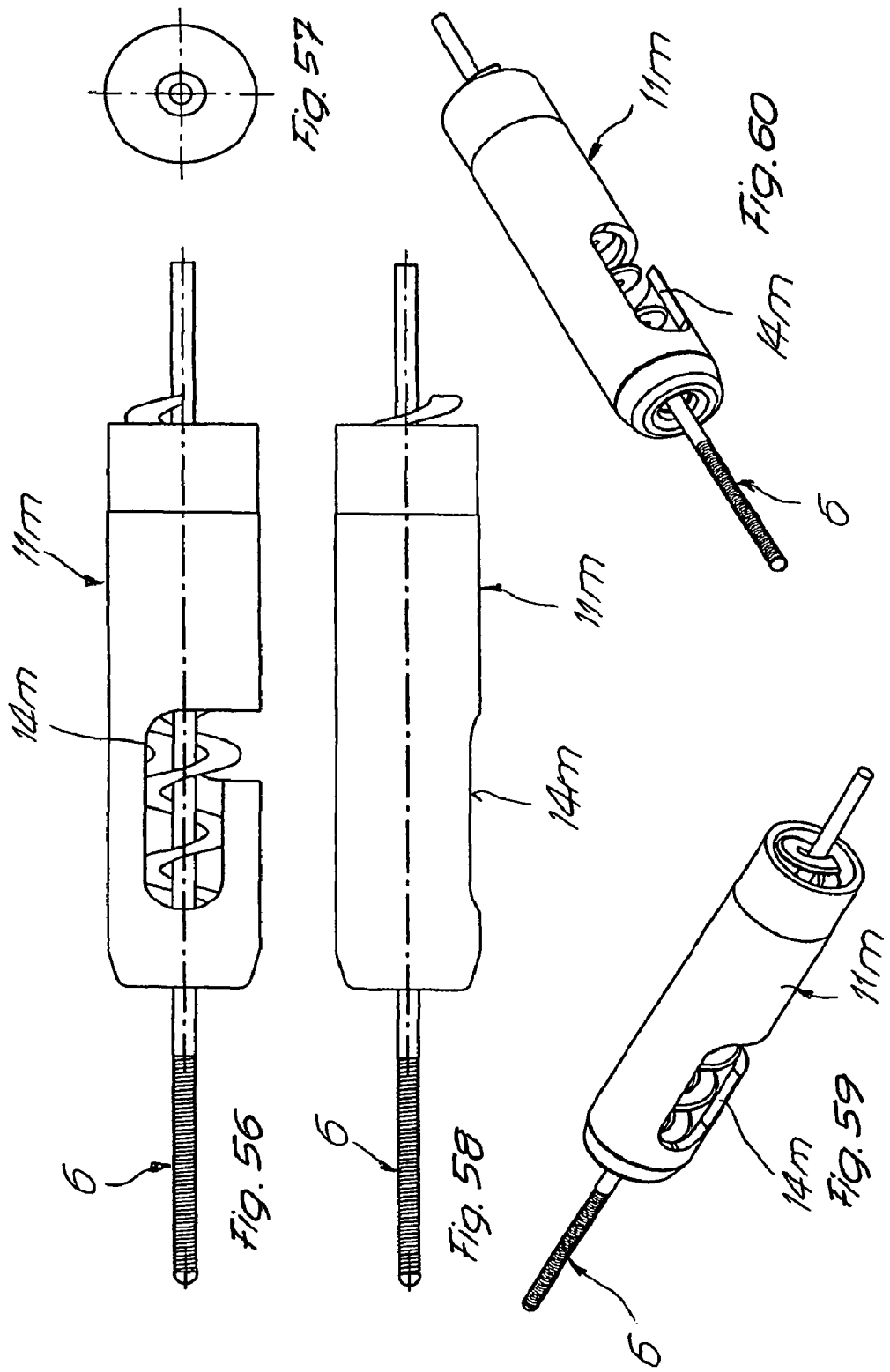

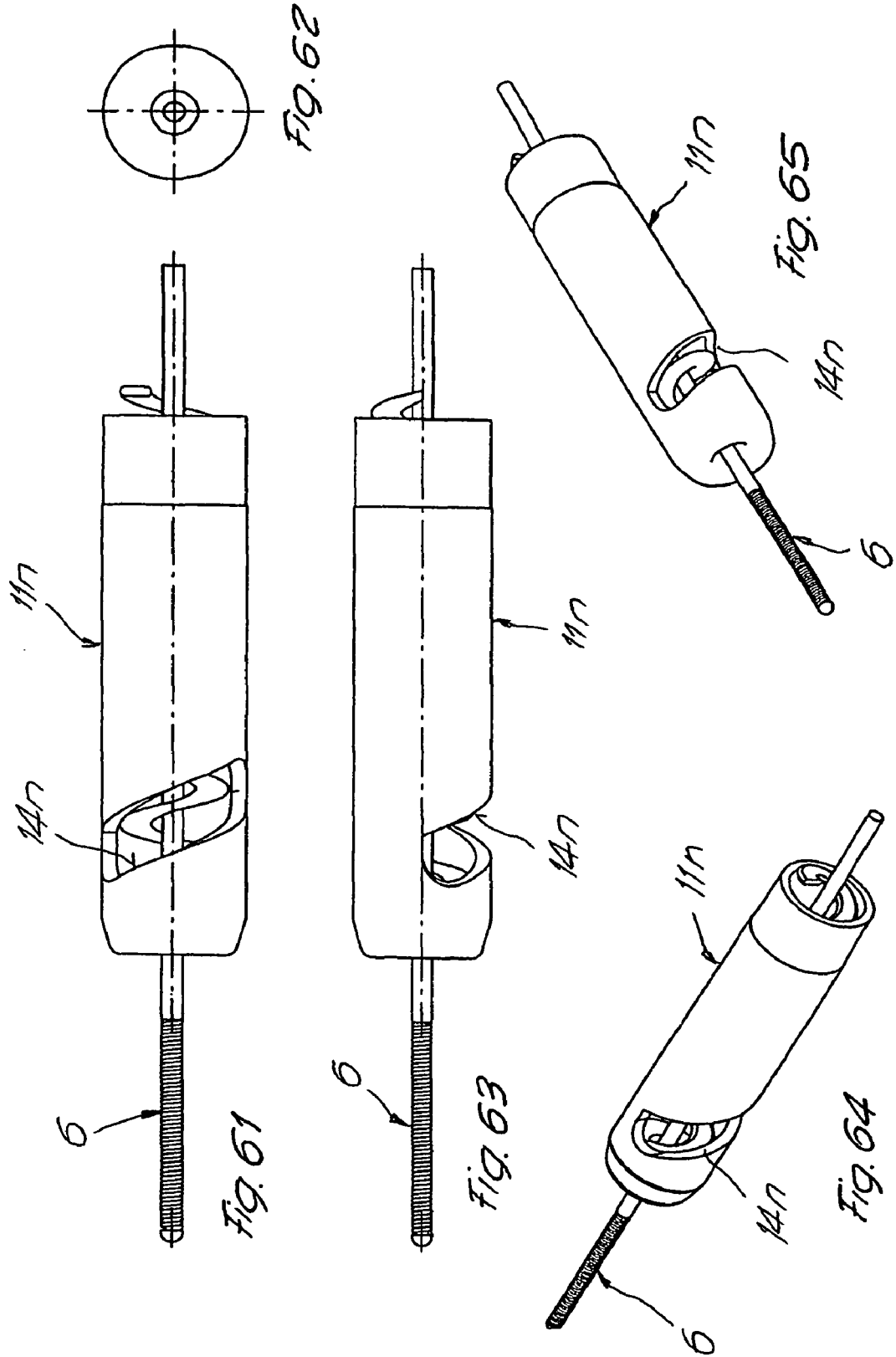

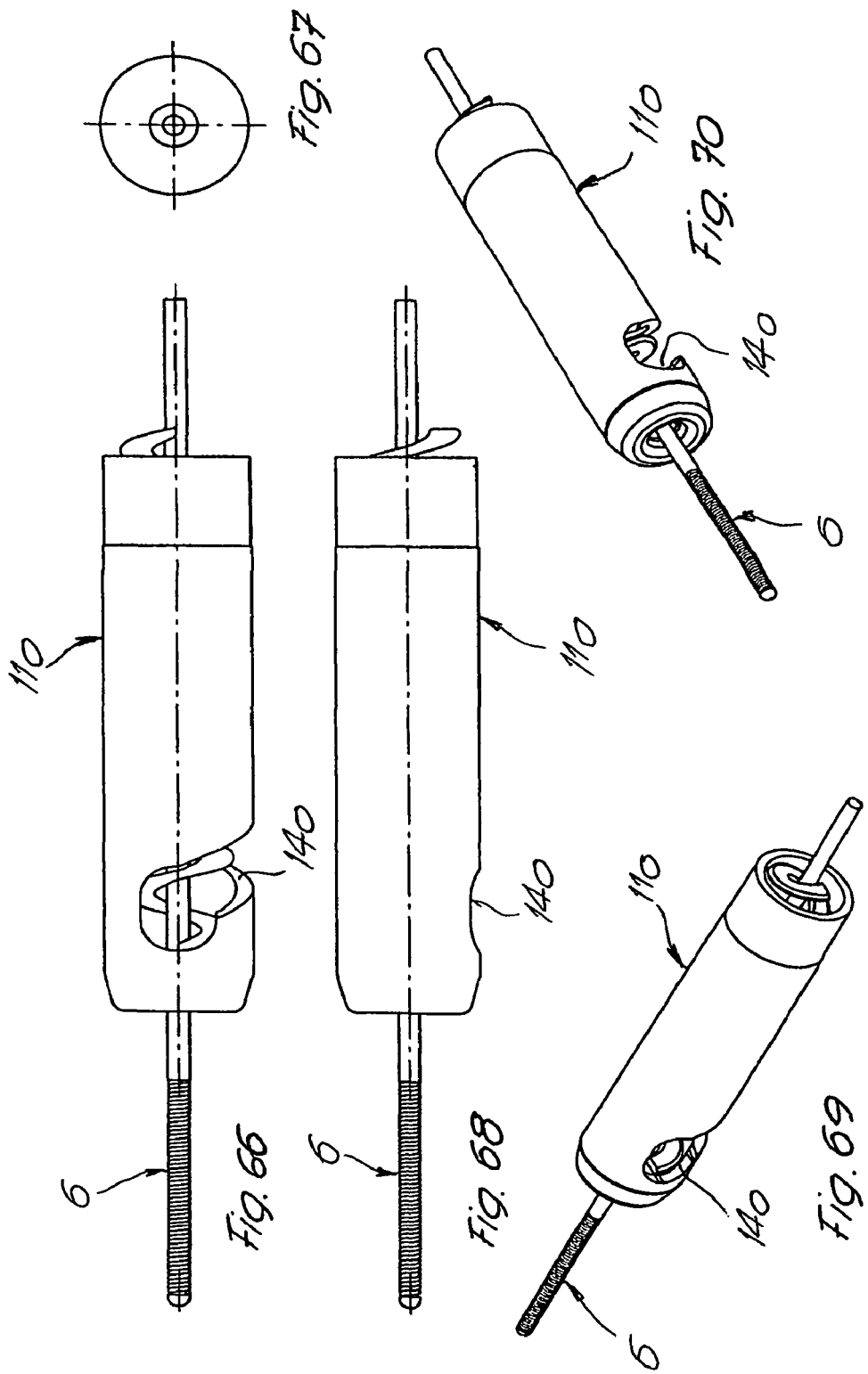

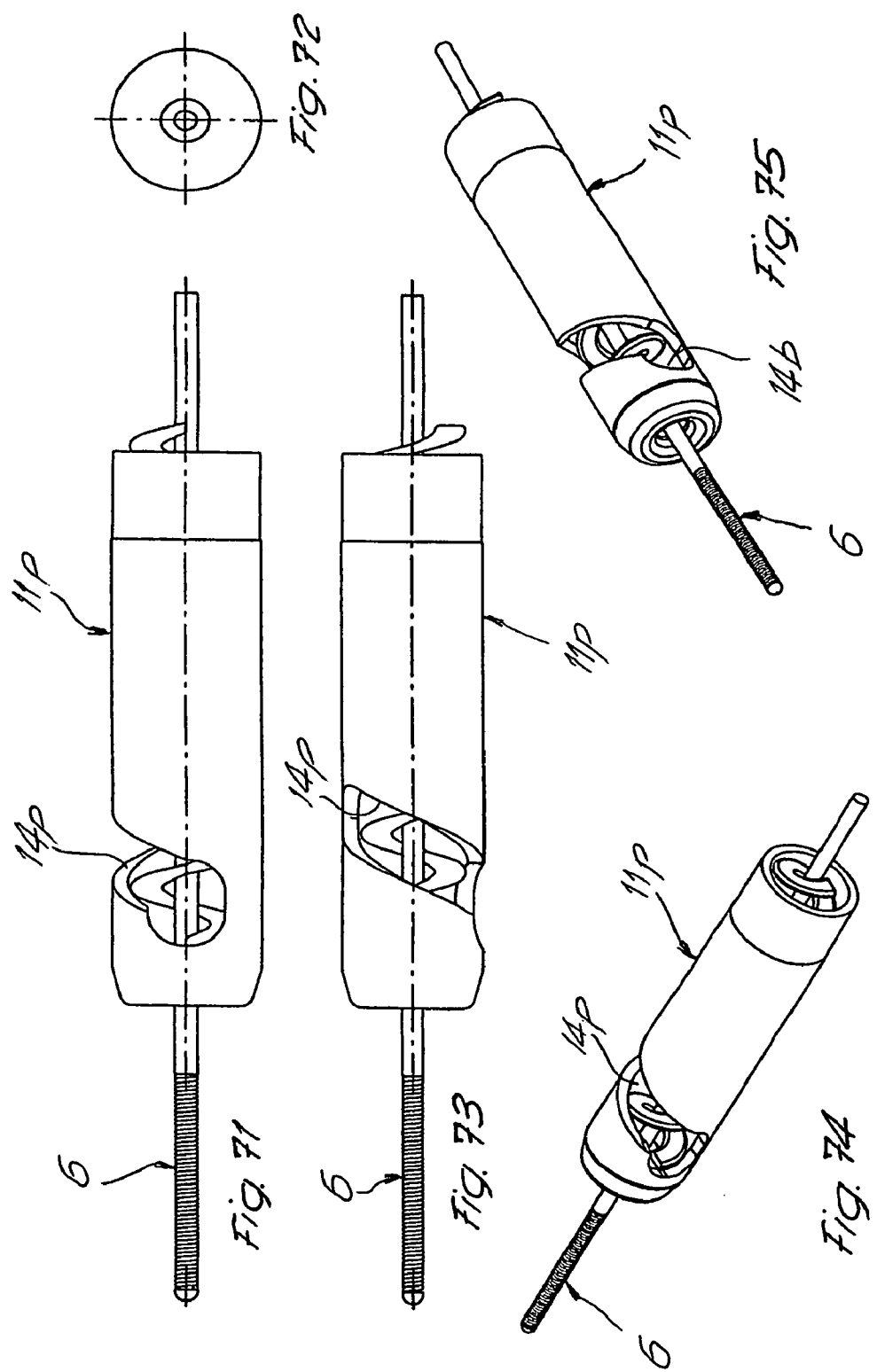

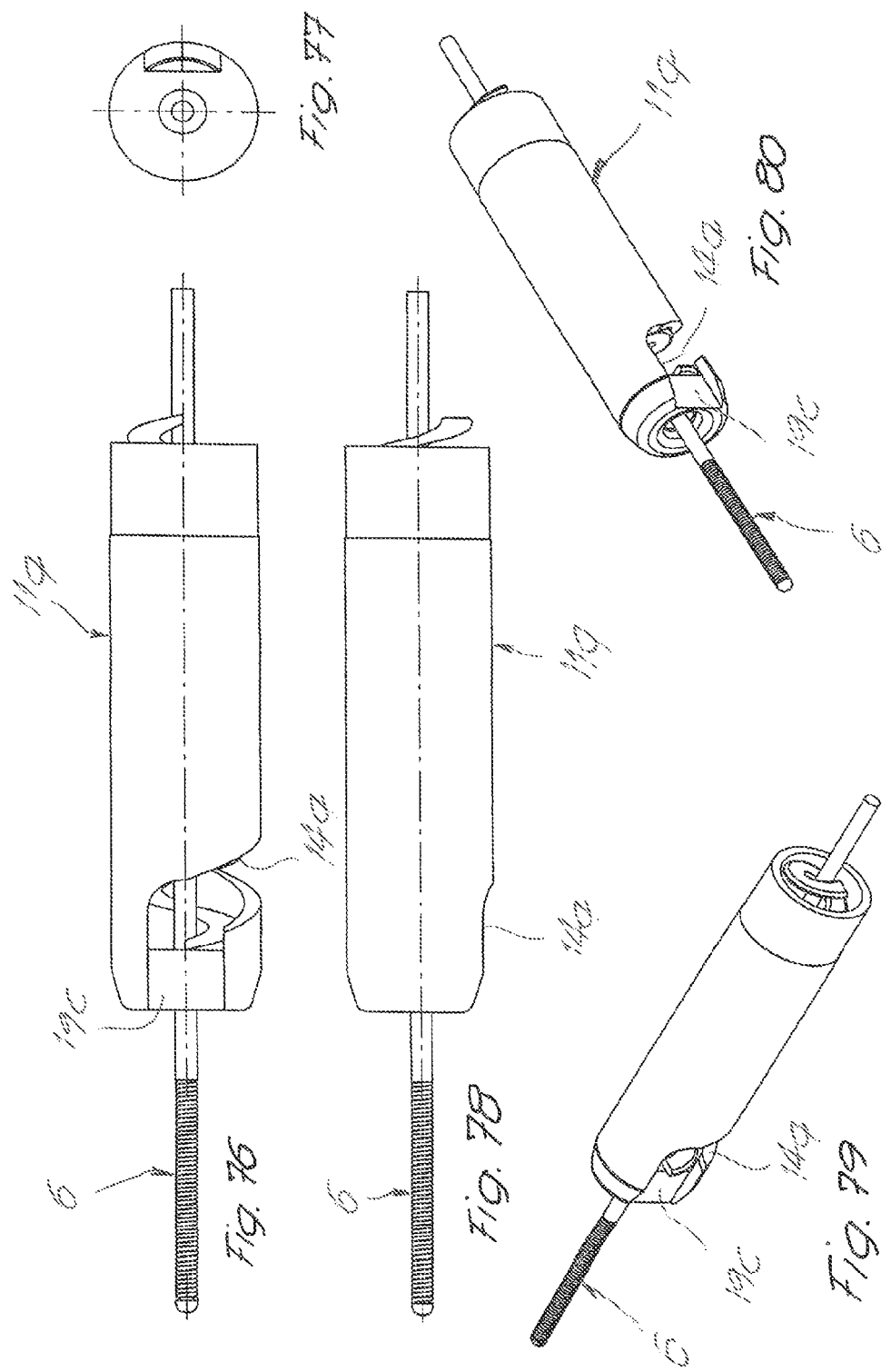

CATHETER FOR ASPIRATING, FRAGMENTING AND REMOVING MATERIAL

This application claims benefit as a Continuation of prior application Ser. No. 10/591,100 having a 371(c) national-stage date of Oct. 25, 2006 and now issued as U.S. Pat. No. 7,905,896 dated Mar. 15, 2011, which in turn is a national-stage entry of prior PCT International application no. PCT/IB2005/00543 filed on Mar. 3, 2005, which claims benefit of priority to prior Swiss national application no. 2176/04 filed on Dec. 22, 2004 and also benefit of priority to prior Swiss national application no. 0369/04 filed on Mar. 4, 2004; the entireties of U.S. application Ser. No. 10/591,100 and of PCT International application no. PCT/IB2005/00543 are expressly incorporated herein by reference in their entirety, for all intents and purposes, as if identically set forth herein.

BACKGROUND

1. Field of the Invention

The invention relates to a catheter for aspirating, fragmenting and removing removable materials from hollow bodies, in particular thrombi and emboli from blood vessels.

2. Description of Related Art

Such catheters are used in particular for the treatment of occlusive arterial diseases by aspiration, fragmentation and removal of emboli and thrombi. They are introduced into the artery or vein and advanced, preferably with X-ray monitoring, up to the narrowed or blocked area that is to be treated. A fragmentation tool drivable in a rotary manner by means of a rotary drive, and a working head, are arranged at their front or distal end.

In the case of these catheters, a distinction should be made as a rule on the basis of two different fields of use:

A) Atherectomy

This is the removal of, as a rule, hard deposits that have adhered to the vessel walls over many years.

B) Thrombectomy

This is the removal of fresh blood clots that accumulate at bottlenecks and lead to blockage of the blood vessels (emboli).

A rotational catheter disclosed, for example, in European pat. no. EP0267539B1 and intended for atherectomy has, as a cutting tool, a substantially ellipsoidal cutter whose surface is provided with abrasive material and that is driven via a flexible drive shaft by a rotary drive arranged at the proximal end of the catheter at a speed of up to 160 000 rpm. The cutter is connected to the flexible drive shaft. The drive shaft runs in a tubular sheath serving as a catheter tube. A guide wire, which is introduced into a blood vessel before the introduction of the catheter, is advanced to the area to be treated or slightly beyond, and serves as a guide for the cutter and the drive shaft extends through the drive shaft.

In the case of these known rotational catheters, the risk that the vessel wall will be injured and in certain circumstances even perforated, particularly in pronounced curves of the blood vessel, cannot be ruled out.

A further rotational catheter disclosed in U.S. Pat. No. 5,571,122 has a cutting tool with a multiplicity of peeling knives extending in the axial direction and driven at a speed of about 800 rpm. By axial compression of the cutting tool, the peeling knives can be caused to bulge radially outward and the external diameter of the cutting tool is thus increased. In the case of this catheter, there is the risk that, particularly as a result of the relatively slow circumferential speed, the peeling knives may pull, drag or jam against the vessel wall, with the result that the blood vessels react dramatically in that they contract and thus prevent further intervention.

U.S. Pat. No. 5,226,909 discloses another atherectomy catheter that has, on its working head, a sleeve-like or helical cutting element drivable by a rotary drive and/or displaceable in the axial direction. The opening of the working head is pressed against the deposits adhering to the vessel wall by means of a lateral inflatable balloon. These deposits are then comminuted by rotation or axial advance of the cutting element and are collected in a chamber. The chamber must then be emptied from time to time by withdrawing the catheter. Continuous removal of comminuted deposited material is not envisaged.

PCT published application no. WO96/29941A1 describes a rotational catheter for atherectomy, whose working head includes a stationary stator, connected to a tube, and a rotor. The rotor is rotatable relative to the stator by means of a high-speed transport/drive screw. Both the stator and the rotor have, at their circumference, windows that can be caused to coincide. As a result of shearing between a cutting edge on the rotor and an opposite cutting edge on the openings of the stator, comminution of the parts projecting into or sucked into the openings is effected. The rotor may surround the stator on the outside ("outer rotor") or may be arranged in the interior of the stator ("inner rotor").

Catheters having inner and outer rotors with cutting edges that operate around the catheter axis have the disadvantage that they stir up blood and occlusion material, so that the blood flow from proximal to distal may wash away particles that may again produce blockages and blood flow problems in other areas of the blood circulation, particularly in small blood vessels.

Some further documents relating to the prior art include EP and PCT publications, EP patents, and U.S. patents having the following numbers: EP0310285A2; EP0448859A2, EP0669106A2, EP0680730A2, EP0669106B1, EP0739603A1, WO02/49690A2, U.S. Pat. No. 4,857,046 and U.S. Pat. No. 5,100,426.

Rotational catheters known to date and comprising revolving knife-like elements or cutters require a relatively powerful rotary drive which in turn necessitates a more powerful rotationally-more-rigid catheter tube for compensating the moment of reaction that arises during cutting of particles, in order that the catheter tube does not rotate about the longitudinal axis. However, a stronger or rotationally-more-rigid tube is inevitably less flexible, with the result that the catheter is in certain circumstances disadvantageous in the curves of blood vessels.

It is the object of the invention to provide a catheter, in particular for thrombectomy, that has no externally revolving cutting knife, cutter or the like, operates in an atraumatic manner and can aspirate and fragment thrombi and emboli in the blood vessel and transport them through the catheter tube continuously out of the vessel.

It is therefore intended to achieve a reduction in components and to minimise the risk of injury to walls of blood vessels. The advantages of known systems, in particular those of the system according to PCT publication no. WO96/29941A1 are however to be retained.

In accordance with one or more embodiments of the present invention, a catheter for aspirating, fragmenting and removing removable materials from hollow bodies, in particular thrombi and emboli from blood vessels, comprises a working head that is axially displaceable over a guide wire independently thereof, is arranged at the distal end of the catheter, and has at least one lateral opening. The catheter also may include: a flexible transport screw, operable to rotate by means of a rotary drive of a drive unit remote from the working head; and a flexible tube, which surrounds the transport screw, connects to the working head, and facilitates removal of the detached thrombi and emboli fragments; and a cutting tool.

According to the invention, the object of the invention is achieved if the transport screw in the region of the working head is in the form of a shearing cutting tool cooperating with the opening of the working head in order to continuously comminute the penetrating materials or aspirated and/or detached thrombi and emboli between the peripheral borders of the transport screw and borders of the openings. The transport effect of the transport screw is retained as in the design according to PCT publication no. WO96/29941A1.

The transport screw thus performs an additional function, namely the comminution of the deposit particles and tissue particles aspirated in the transport direction into the openings by the action of the reduced pressure. In contrast to the prior art, this comminution takes place not rhythmically when cutting edges come into contact with one another but continuously. The internally rotating and internally cutting transport screw in the working head aspirates and comminutes the deposits without causing vortices outside. The risk that particles will be washed away and that there will be blood flow disturbances distally due to catheter intervention is therefore absent.

There are also virtually no vibrations, which in principle are desirable to avoid in the case of blood vessels. Since a lower reaction torque is necessary as a result of the continuous cutting, the tube may also have a thinner wall and be more elastic. This is also the case in particular because the cutting force generated during fragmentation acts mainly in the axial direction (proximally) and not, as in the prior art described, in the circumferential direction. The torsional load of the tube is therefore very small.

The working head is preferably, as shown, cylindrical, having one or more window-like openings, such as bores or shaped slots, arranged at the circumference. As a result of the cooperation of the high speed rotating transport screw and the inner wall of the cylindrical working head, or the edges of the openings, a rotary cutting tool is provided that has good fragmentation power with a relatively low torque or low drive power.

Compared with the prior art disclosed in PCT publication no. WO96/29941A1, at least one of the components of the working head, namely the rotor, is omitted. This leads to a simplification and cost reduction. Furthermore, because of the lack of a rotor, jamming between rotor and stator cannot occur. In addition the design according to the invention permits the reduction of the external diameter to small dimensions not realizable to date. Such small dimensions are required, for example, for the treatment of coronary vessels.

The transport screw is expediently formed, in the region of the working head, as a shearing cutting tool that cooperates with the opening of the working head and, in the operating state, continuously comminutes the penetrating materials or aspirated and/or detached thrombi and emboli between the peripheral borders of the transport screw and borders of the opening, and removing said materials or thrombi or emboli along the transport surface in the direction of the proximal end.

The transport screw is, in the region of the working head, advantageously in the form of a shearing cutting tool that cooperates with the opening of the working head and, in the operating state, continuously comminutes the penetrating material or aspirated and/or detached thrombi and emboli between the peripheral borders of the transport screw and borders of the openings, and removing said materials or thrombi or emboli along the transport surface. The lateral opening of the working head is in the form of an L-shaped slot having a limb extending substantially in the longitudinal direction and a limb extending along a part of the circumference. The thrombi and emboli to be removed can therefore be drawn in or sucked along the limb extending in the longitudinal direction into the interior of the working head and then sheared off by means of the transport screw at the proximal edge of the limb extending in the circumferential direction.

The ratio of the width of the limb, extending in the longitudinal direction, to the width of the limb, extending in the circumferential direction is from 1.0 to 1.3. Thus, good transport of the aspirated thrombi and emboli in the direction of the proximal end and subsequent clean shearing off are permitted.

The distal part of the transport screw, in the region of the working head, is formed in the external diameter to be an exact fit with the internal diameter of the preferably cylindrical working head, so that the external diameter of the transport screw results in only minimal diameter play relative to the inner lateral surface of the working head. This prevents fragmented elements from being able to become jammed between the transport screw and the internal diameter of the working head.

The edges on the outside of the transport screw are advantageously formed so as to be sharp in the region of the opening of the working head. This permits a good and clean shearing off of generally very tough thrombi and emboli to be removed.

The working head is expediently tapered toward its distal end. This ensures that the catheter can also be advanced by sliding in narrow radii of curvature of the vessels without great resistance. Thus, it cannot become hitched to the vessel wall or to projections.

The edges of the lateral openings are advantageously formed to be sharp at least in regions on the inside. This together with the periphery of the transport screw permits a clean shearing process for fragmenting the thrombi or emboli. The openings of the catheter head are designed so that the transport screw rotating at high speed fragments thrombi and emboli that are aspirated at the inner sharp edges of the openings and the outer diameter of the transport screw to form pieces. These pieces are transported in the direction of the rotary drive by the prevailing suction and the screw transport.

The edges of the lateral opening are rounded, expediently at least in regions, on the lateral surface of the working head. This permits vortex-free flow of the deposits to be removed and of other body fluids in the region of the working head.

The lateral opening in the working head is advantageously in the form of a slot. Slots can be easily produced and can be adapted to requirements in their dimensions.

It is expedient if the slot runs at least partly in the axial direction of the working head. By changing length and width, the slot can be adapted according to the different requirements of the different applications.

An advantageous embodiment includes the slot being formed, relative to the longitudinal axis of the working head, at least partly along a helix. Optimum adaptation to the respective circumstances is also possible by means of the helix angle or the direction of rotation of the helix. The direction of rotation of the helix can be identical to or different from the direction of rotation of the transport screw. An identical direction of rotation gives a drawn out cut over a larger cutting length. This is advantageous in particular for tough or fibrous material to be removed. An opposite direction of rotation gives a short cut and tends to be suitable for brittle material.

For certain applications, it is expedient if the width of the slot decreases toward the proximal end of the working head. The deposits sucked in to the slot, such as thrombi or emboli, are thus forced toward the proximal end against a bottle neck, which permits improved fragmentation of the deposits.

An advantageous embodiment includes forming the slot as an L-shape. The slot may include, for example, a part running in the axial direction and a part connected to this and running in the circumferential direction.

Expediently, at least one groove-like recess starting from the distal end and opening into the lateral opening is formed in the distal end region of the working head. This groove-like recess forms a channel through which thrombi, emboli and/or other deposits can therefore also be aspirated from the distal end, can reach the region of the lateral opening and can be comminuted by the cooperation of the transport screw with the working head.

It is advantageous if the depth of the groove-like recess increases toward the proximal end of the working head. This can be achieved on the one hand if the working head tapers toward the distal end or if the base surface of the recess is arranged so as to be inclined relative to the longitudinal axis of the working head. As a result of the increasing depth, the flow cross-section is increased toward the proximal end and hence the deposits are more easily transported away.

The width of the groove-like recess is expediently greater than the chord of the internal diameter of the working head in the region of the groove base. This gives rise to clean edges, along which the deposits are sucked into the interior of the working head in order to be subsequently fragmented there.

The working head is advantageously connected to the tube axially so as to be resistant to tension and pressure. Since in practice only a small reaction torque is exerted on the tube, in contrast to the prior art, the requirements with regard to the connection between the working head and the tube and with regard to the torsional rigidity of the tube itself are relatively low so that, for example, a simple press-fit or adhesive connection is possible and the tube may be very elastic.

As a result of the flow caused by the transport screw, reduced pressure results in the tube. In order to increase the flexibility of the tube, it is expedient if the tube has a reinforcement at least in sections. As a result of the reinforcement, the wall thickness of the tube can also be kept thinner and the flexibility can thus also be increased. A reinforcement also has a stabilizing effect on the play between the inner wall of the tube and the external diameter of the transport screw.

The reinforcement is advantageously in the form of a metallic helix. Such a helix has a high flexibility in the bending direction and good tensile and compressive strength.

For production and also for use during insertion of the catheter, it is expedient to arrange the reinforcement on the inside of the tube. This permits a smooth surface on the outside of the catheter. However, the reinforcement can also be embedded completely in plastic.

An advantageous embodiment includes forming the tube in two parts, the proximal part being in the form of a pure plastic tube and the distal part facing the working head being in the form of a metallic helical spring having a thin-walled elastic plastic sheath. Thus, the distal part of the tube is particularly flexible and the catheter can be advanced and withdrawn virtually without effort even around narrow curves.

The working head and/or the transport screw expediently comprises metal. In particular, stainless steels or other corrosion-resistant alloys are suitable.

With regard to improved material properties, the working head can alternatively also be composed of sintered ceramic or metal ceramic or have a highly resistant layer for protection from wear.

Further developments of the invention and variants thereof are indicated in the dependent patent claims and in the figures and the description of the drawings.

It is true that in the above text reference is made to a catheter for aspiration, fragmentation and removal, in particular from human blood vessels; however, the invention is not limited thereto but rather is also available to other users for analogous applications in the medical sector (e.g. reopening occluded organ regions, such as, for example, ureter, bile duct or fallopian tube and vascular prostheses and so-called stents). The patent claims should accordingly be interpreted broadly.

The list of reference numerals and the drawing together with the subject matter described or protected in the claims, form integral parts of the disclosure of this Application.

The figures are described in relation to one another and overall. Identical reference numerals denote identical components, and reference numerals with different indices indicate functionally identical components.

DESCRIPTION OF THE DRAWINGS

The figures show the following by way of example:

FIG. 2 shows a view of the working head of a catheter according to FIG. 1;

FIG. 3 shows the working head according to FIG. 2, in longitudinal section;

FIGS. 4 and 5 show a variant of the working head in perspective view;

FIGS. 6 to 10 show a variant of the working head with a rectangular lateral opening;

FIGS. 11 to 15 show a variant of the working head according to FIGS. 6 to 10, with a narrow slot extending in the longitudinal direction;

FIGS. 16 to 20 show a variant of the working head with an approximately square lateral opening;

FIGS. 21 to 25 show a variant of the working head with a slot-like opening extending in the circumferential direction;

FIGS. 26 to 30 show a variant of the working head with a groove-like recess starting from the distal end and opening into the lateral opening;

FIGS. 31 to 35 show a variant of the working head with a lateral opening in the form of a longitudinal slot and a groove-like recess starting from the distal end and opening into the lateral opening;

FIGS. 36 to 40 show a variant of the working head with an approximately triangular lateral opening whose width tapers toward the proximal end;

FIGS. 41 to 45 show a variant of the working head with a lateral opening which consists of a region extending in the axial direction and a region extending over a part of the circumference;

FIGS. 46 to 50 show a variant of the working head analogously to FIGS. 41 to 45, the region extending over a part of the circumference running in the opposite direction;

FIGS. 51 to 55 show a variant of the working head analogously to FIGS. 41 to 45, the region extending in the longitudinal direction being substantially longer;

FIGS. 56 to 60 show a variant of the working head analogously to FIGS. 51 to 55, the region extending over a part of the circumference running in the opposite direction according to the setup according to FIGS. 51 to 55;

FIGS. 61 to 65 show a variant of the working head with a lateral opening extending along a helix;

FIGS. 66 to 70 show a variant of the working head analogously to FIGS. 61 to 65, that region of the opening which runs along a helix opening at the distal end into a region running in the axial direction;

FIGS. 71 to 75 show a variant of the working head analogously to FIGS. 66 to 70, that region of the opening which runs along a helix being oriented in the opposite direction of rotation; and, FIGS. 76 to 80 show a variant of the working head analogously to FIGS. 66 to 70, a groove-like recess starting from the distal end opening into the opening running along a helix.

FIG. 1 schematically shows the overall setup of a medical device for use of the catheter according to the invention. The device has a drive unit 1 with a rotary drive 2. An injection chamber 3 is present at the front end of the rotary drive. This is connected via a removal channel 4 to a collecting container 5. A guide wire 6 passing through the drive unit has a proximal (rear) end 7 and a distal (front) end 8. A movable insertion lock 9 is located upstream of the injection chamber 3. This setup corresponds substantially to that of PCT publication no. WO96/29941A1. Design details can also be taken over from that reference, which comprises part of the knowledge of a person of ordinary skill in the art.

Figure 1:
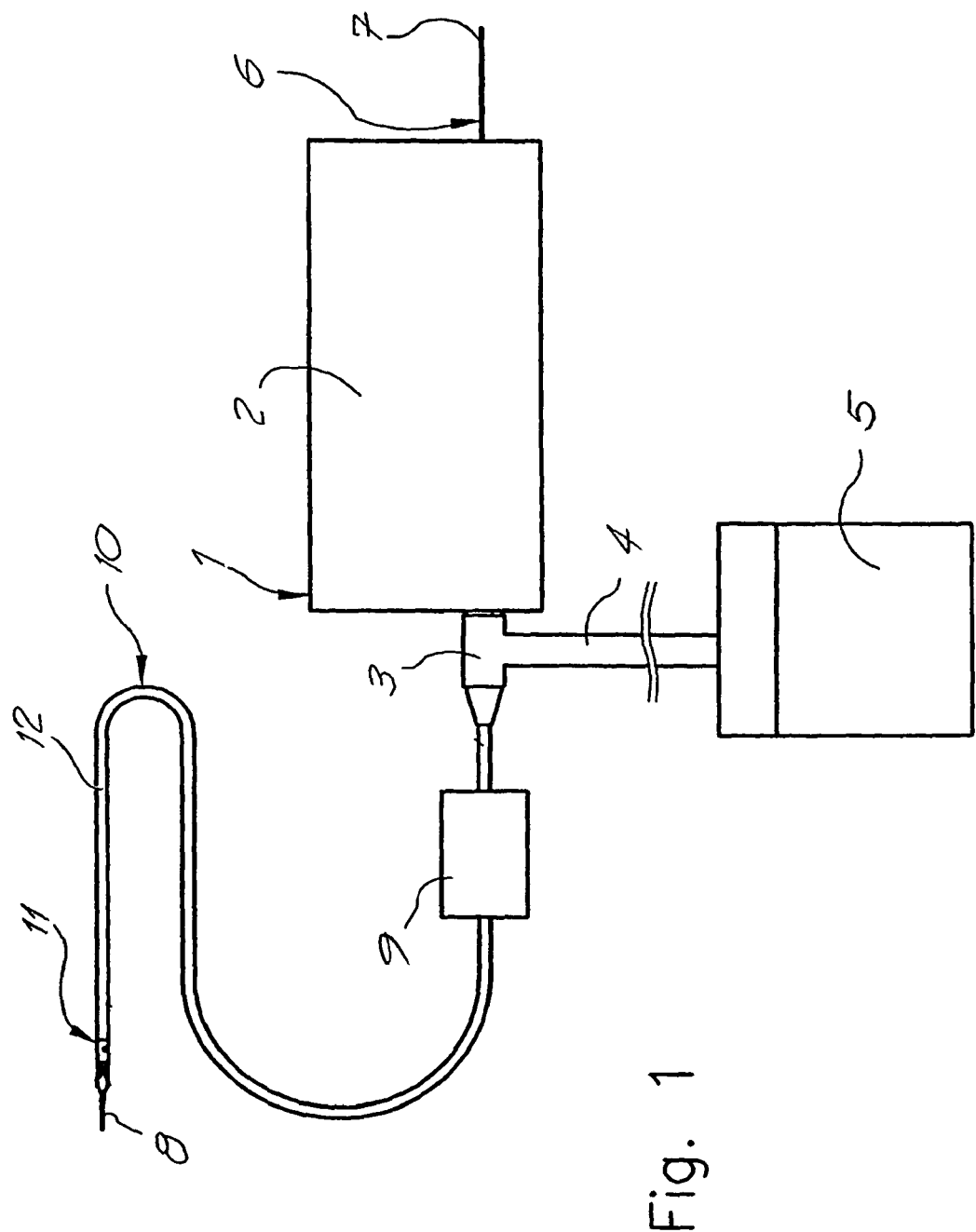
FIG. 1 shows the schematic overall setup of a device having a catheter according to the invention.

A catheter designated as a whole by 10 substantially comprises a flexible tube 12 and a working head 11 connected thereto in a manner resistant to tension and pressure. The guide wire 6 passes through the catheter 10, the distal end 8 projecting beyond the working head 11.

The working head 11a visible in FIGS. 2 and 3 and shown on a larger scale and partially in section has a lateral opening 14a. A helical transport screw 13 surrounds the guide wire 6 and is matched in external diameter exactly to the internal diameter of the working head 11a. The opening 14a has an inner edge 15 that is sharp and an outer border 16 that is rounded. At the edge 15, the deposits that are sucked by the reduced pressure generated by the transport screw 13 into the interior of the working head 11a are fragmented by shearing off by the periphery of the transport screw 13 which cooperates with the edge 15 and are transported by means of the transport screw 13 in the direction of the drive unit 1 through the tube 12.

The section shown in FIG. 3 shows the setup of the tube 12. This preferably comprises a reinforcement 17 wound, for example, from a fine wire and a thin plastic sheath 18. This setup gives very high flexibility of the tube 12, which is advantageous particularly in the distal region of the catheter 10. For production and cost reasons, the proximal region of the tube can also be in the form of a customary thicker plastic tube, it being possible for the two regions to be connected to one another, for example, by shrinkage or adhesive bonding. One variant comprises the joint covering of the reinforcing tube and of the connecting proximal part of the tube with a thin, closely fitting covering.

The working head 11b shown in FIGS. 4 and 5 has an opening 14b that substantially comprises a longitudinal slot 20 and a circumferential slot 21 extending along a part of the circumference. A groove-like recess 19a starting from the distal end opens into the longitudinal slot 20. This formation makes it possible to handle the deposits in front of the working head 11b. The working head 11b tapers toward the distal end. This facilitates the advance of the catheter in the duct or blood vessel to be freed from obstruction.

FIGS. 6 to 80 show different variants of the formation of the lateral opening in the working head. However, these diagrams are not limiting but are to be understood merely by way of example. Further embodiments and also combinations of the formations shown are conceivable.

LIST OF REFERENCE NUMERALS

1 Drive unit
2 Rotary drive
3 Injection chamber
4 Removal channel
5 Collecting container
6 Guide wire
7 Proximal end
8 Distal end
9 Insertion lock
10 Catheter
11a-11q Working head
12 Tube
13 Transport screw
14a-14q Lateral Opening
15 Edge
16 Border
17 Reinforcement
18 Sheath
19a-19c Groove-like recess
20 Longitudinal slot
21 Circumferential slot

What is claimed is:
1. A catheter comprising:
a flexible tube, said flexible tube having a proximal end, said flexible tube having a distal end;
a working head, said working head having a proximal end, said working head having a distal end, said proximal end of said working head being connected to said distal end of said tube;
said working head having a cylindrical bore open from said proximal end of said working head, said working head having an end wall spanning and capping said cylindrical bore at said distal end of said working head;
a guide wire extending through said tube and through said cylindrical bore, and said guide wire extending out of a hole in said end wall of said working head;
a flexible transport screw extending from said proximal end of said tube through said tube to said distal end of said working head, said flexible transport screw provided with helically extending transport surfaces;
said flexible transport screw connected to a rotary drive configured to rotate said flexible transport screw;
said flexible transport screw having a proximal end, and said flexible transport screw having a distal end configured to rotate relative to said end wall, wherein said distal end abuts said end wall;
said flexible transport screw having a distal part disposed in said cylindrical bore, said flexible transport screw distal part forming a helix, said helix having an external diameter fitting the diameter of said cylindrical bore to rotate therein in contact therewith;
said flexible transport screw distal part having sharp edges;
a first lateral opening in said working head, said first lateral opening having internal edges cooperating with said flexible transport screw distal part edges to shear and comminute material;
said flexible tube distal end having a proximate flexible tube distal end portion, said flexible tube distal end por- tion including a helical spring, said helical spring encased in a thin-walled plastic sheath; and,
said flexible tube distal end portion is connected to said working head proximal end.

2. The catheter as claimed in claim 1, wherein:
said helix external diameter exactly fits said cylindrical bore's diameter to permit only minimal diameter play.

3. A catheter as claimed in claim 1, further comprising:
said working head has an external surface, and said working head external surface tapers at said working head distal end.

4. The catheter as claimed in claim 1, wherein:
said first lateral opening internal edges are sharp.

5. A catheter as claimed in claim 1, further comprising:
said working head has an external surface;
said first lateral opening has external edges at said external surface; and, said external edges are rounded.

6. The catheter as claimed in claim 1, wherein:
said lateral opening is a slot.

7. The catheter as claimed in claim 6, wherein:
said slot runs at least partially in an axial direction of said working head.

8. The catheter as claimed in claim 6, wherein:
said slot is formed at least partly along a helix relative to a longitudinal axis of said working head.

9. The catheter as claimed in claim 6, wherein:
said slot has width decreasing towards a proximal end of said working head.

10. The catheter as claimed in claim 6, wherein:
said slot is formed in an L-shape.

11. A catheter as claimed in claim 1, further comprising:
said working head has a distal end region proximate to said working head distal end;
said working head has an external surface; and,
a groove-like bottomed recess in said working head external surface, said groove-like recess extending from said working head distal end region to open into said lateral opening.

12. The catheter as claimed in claim 11, wherein:
depth of said groove-like bottomed recess increases in the direction from said working head distal end to said working head proximal end.

13. The catheter as claimed in claim 11, wherein:
a width of said groove-like bottomed recess is greater than a chord of an internal diameter of said working head.

14. The catheter as claimed in claim 11, wherein:
said lateral opening is a slot; and,
said slot is formed at least partly along a helix relative to a longitudinal axis of said working head.

15. The catheter as claimed in claim 1, wherein:
the connection between said flexible tube distal end portion and said recess in said working head proximal end resists tension and pressure.

16. A catheter as claimed in claim 1, further comprising:
at least one tube reinforcement in said flexible tube.

17. The catheter as claimed in claim 16, wherein:
said tube reinforcement is a metallic helix.

18. The catheter as claimed in claim 16, wherein:
said tube reinforcement is arranged on an inside of said tube.

19. The catheter as claimed in claim 1, wherein:
said working head is made of metal.

20. The catheter as claimed in claim 1, wherein:
said flexible transport screw is made of metal.

21. The catheter as claimed in claim 1, wherein:
said working head includes ceramic material.

22. A catheter comprising:
a flexible tube, said flexible tube having a proximal end, said flexible tube having a distal end;
a working head, said working head having a proximal end, said working head having a distal end, said proximal end of said working head being connected to said distal end of said tube;
said working head having a cylindrical bore open from said proximal end of said working head, said working head having an end wall spanning and capping said cylindrical bore at said distal end of said working head;
a guide wire extending through said tube and through said cylindrical bore, and said guide wire extending out of a hole in said end wall of said working head;
a flexible transport screw extending from said proximal end of said tube through said tube to said distal end of said working head, said flexible transport screw provided with helically extending transport surfaces;
said flexible transport screw connected to a rotary drive configured to rotate said flexible transport screw;
said flexible transport screw having a proximal end, and said flexible transport screw having a distal end configured to rotate relative to said end wall, wherein said distal end abuts said end wall;
said flexible transport screw having a distal part disposed in said cylindrical bore, said flexible transport screw distal part forming a helix, said helix having an external diameter fitting the diameter of said cylindrical bore to rotate therein in contact therewith;
said flexible transport screw distal part having sharp edges;
a first lateral opening in said working head, said first lateral opening having internal edges cooperating with said flexible transport screw distal part edges to shear and comminute material, said helical transport surfaces removing material in a direction towards the proximal end of said tube;
said flexible tube distal end having a proximate flexible tube distal end portion, said flexible tube distal end portion including a helical spring, said helical spring encased in a thin-walled plastic sheath; and,
said flexible tube distal end portion is connected to said working head proximal end.

23. A catheter comprising:
a flexible tube, said flexible tube having a proximal end, said flexible tube having a distal end;
a working head, said working head having a proximal end, said working head having a distal end, said proximal end of said working head being connected to said distal end of said tube;
said working head having a cylindrical bore open from said proximal end of said working head, said working head having an end wall spanning and capping said cylindrical bore at said distal end of said working head;
a guide wire extending through said tube and through said cylindrical bore, and said guide wire extending out of a hole in said end wall of said working head;
a flexible transport screw extending from said proximal end of said tube through said tube to said distal end of said working head, said flexible transport screw provided with helically extending transport surfaces;
said flexible transport screw connected to a rotary drive configured to rotate said flexible transport screw;
said flexible transport screw having a proximal end, and said flexible transport screw having a distal end configured to rotate relative to said end wall, wherein said distal end abuts said end wall;

said flexible transport screw having a distal part disposed in said cylindrical bore, said flexible transport screw distal part forming a helix, said helix having an external diameter fitting the diameter of said cylindrical bore to rotate therein in contact therewith;

said flexible transport screw distal part having sharp edges;

a first lateral opening in said working head, said first lateral opening forming an L-shaped slot, said slot having a first limb extending substantially in a longitudinal direction and said slot having a second limb extending along a part of a circumference, said first lateral opening having internal edges cooperating with said flexible transport screw distal part edges to shear and comminute material;

said flexible tube distal end having a proximate flexible tube distal end portion, said flexible tube distal end portion including a helical spring, said helical spring encased in a thin-walled plastic sheath; and, said flexible tube distal end portion is connected to said working head proximal end.

24. The catheter as claimed in claim 23, wherein:

a ratio of a width of the first limb extending in the longitudinal direction to a width of the second limb extending along a part of a circumference is from 1.0 to 1.3.

* * * * *